United States Patent
Muntermann

(10) Patent No.: US 6,461,289 B1
(45) Date of Patent: Oct. 8, 2002

(54) DEVICE FOR MAGNETIC FIELD THERAPY

(76) Inventor: Axel Muntermann, Sudetenstrasse 7-9, D-35583 Wetzlar (DE)

( * ) Notice: Subject to any disclaimer, the term of this patent is extended or adjusted under 35 U.S.C. 154(b) by 0 days.

(21) Appl. No.: 09/529,698

(22) PCT Filed: Oct. 16, 1998

(86) PCT No.: PCT/DE98/03033
§ 371 (c)(1), (2), (4) Date: Jun. 22, 2000

(87) PCT Pub. No.: WO99/20345
PCT Pub. Date: Apr. 29, 1999

(30) Foreign Application Priority Data
Oct. 17, 1997 (DE) .................... 297 18 337 U

(51) Int. Cl.[7] .............. A61N 2/00; A61N 1/00
(52) U.S. Cl. ............................ 600/9; 600/13
(58) Field of Search ............... 128/897; 600/9, 600/13; 435/173.5; 606/13

(56) References Cited

U.S. PATENT DOCUMENTS

| | | | |
|---|---|---|---|
| 4,818,697 A | * 4/1989 | Liboff et al. | 435/173.5 |
| 4,932,951 A | * 6/1990 | Liboff et al. | 600/13 |
| 5,106,361 A | * 4/1992 | Liboff et al. | 600/13 |
| 5,312,534 A | 5/1994 | Liboff et al. | |
| 5,441,495 A | 8/1995 | Liboff et al. | |
| 5,450,859 A | * 9/1995 | Litovitz | 128/897 |
| 5,752,911 A | * 5/1998 | Canedo et al. | 600/9 |
| 5,935,054 A | * 8/1999 | Loos | 600/9 |

FOREIGN PATENT DOCUMENTS

| | | |
|---|---|---|
| DE | 42 21 739 A1 | 1/1993 |
| EP | 0 407 006 A1 | 4/1990 |
| WO | WO 96/39493 | 12/1996 |

* cited by examiner

Primary Examiner—Eric F. Winakur
Assistant Examiner—Nikita R Veniaminov

(57) ABSTRACT

The invention relates to a device for magnetic field therapy of human, animal or plant tissue. The invention comprises at least one unit for generating a magnetic field with a statical component which is constant in time and an alternating field component at the location of the tissue which is to be treated. The magnetic alternating field has a predetermined cell biorhythm frequency $v_2$ and is essentially monochromatic. The inventive device additionally comprises a unit for amplitude modulation of the magnetic alternating field with a modulation frequency $v_0$.

17 Claims, 4 Drawing Sheets

DEVICE FOR MAGNETIC FIELD THERAPY

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The invention relates to a device for magnetic field therapy of human, animal, and plant tissues, their organs or cell groups, and includes at least a device for the production of a magnetic field with a static and an alternating field component at the location of the tissue to be treated.

TECHNICAL FIELD

Curative, and also prophylactic, magnetic field treatment is well known in the art. While the tissue to be treated was originally exposed to the magnetic field of a permanent magnet, coils through which current flows are now frequently used for the production of the fields. In European Patent EP 0594655B1, for example, a device with a generator producing an electrical current pulsed with a low frequency and connected to a transmitting coil is disclosed, whose electromagnetic fields act on a region of the body to be treated. In order to provide a device for the transport of ions and particularly of protons, making possible a targeted action on ionic mobility in optional body regions in humans and animals, the transmitting energy for the transmitting coil is chosen to be so high that the energy induced in the electrolyte liquid increases the thermal energy and nevertheless lies within the boundary values of a so-called cell-specific amplitude window. The pulsed currents produced by the generator include a base current pulse of about 100–1000 Hz, which consists of the superposition of a rectangular current and a current which rises about exponentially, followed by a pulse pause of at least equal length. The amplitude of the base pulse train is modulated in amplitude with a modulating frequency of 0.5–25 Hz, and the modulated base pulse train is emitted as a pulse train series for a period of 0.3–1 second, respectively followed by a pulse pause of 0.7–0.5 seconds. The patentee refers to the combined action of pulse frequency, pulse form, pulse energy, and transmission pulse shape, which make possible for ions, and protons in particular, to be targeted and directly injected, for example from the blood, the lymph, or the [tissue] fluid, into the vessel walls and membranes which surround them.

A device is disclosed in U.S. Pat. No. 48,186 for the amplification of the transport of a selected ion through a bio-molecular membrane, which is disposed in a space which is acted on by a local magnetic field. The associated process includes the steps of the production of a magnetic field which has a non-vanishing average value, and the production of a magnetic alternating field with a frequency which corresponds to the cyclotron resonance frequency of the predetermined ion. Due to the energy transfer, which can be controlled by means of the cyclotron resonance frequency, to the predetermined ion, the transport of the ion through the bio-molecular membrane, for example, a cell membrane, can be controlled. In European Patent EP 0407006B1, the same inventors describe a device for the movement of a predetermined ion through a membrane, wherein the frequency of the alternating magnetic field ia proportional to the cyclotron resonance frequency of the predetermined ion, and, differing from the abovementioned American Patent Application, the proportionality constant is a predetermined, odd integer greater than unity.

The devices described hereinabove, by which in detail the internal energy of the intracorporeal electrolyte liquids is increased or the transport of predetermined ions through cell membranes is controlled, exhibit a certain workability in the field of clinical researches.

However, the need further exists to act more effectively on the tissue, and in particular to take account of the specific structure of a living organism in the construction of a device for magnetic field therapy.

BRIEF SUMMARY OF THE INVENTION

The object of the invention set out in this manner is attained surprisingly simply with a device for magnetic field therapy of human, animal, or plant tissues which includes at least a device for the production of a magnetic field with a static component which is constant in time and an alternating field component at the location of the tissue to be treated, characterized in that the magnetic alternating field has a predetermined cell biorhythm frequency $v_z$ and is substantially monochromatic, and the device furthermore includes a device for the amplitude modulation of the magnetic alternating field with a modulation frequency $v_o$ which is determined by the expression $v_o = Bq/2\delta m$, wherein B is the static magnetic flux density, q is the charge and m the mass of the predetermined ion, or is a predetermined organ biorhythm frequency.

All processes in the body take place on the cellular level. Attention has to be paid to the behavior of the body as a whole, as an ordered cell agglomeration.

All living organisms are formed by various cells.

All organs are formed from specific kinds of cells.

All processes in the body of the living organism take place on the cellular level.

All disorders of the living organism begin from the cellular level and go along the following chain: cells→organs→organism.

Disturbances of the ion transport also take place on the cellular level.

Magnetic field therapy is based on the employment of static and alternating magnetic fields, and exerts a direct influence on the living organism and biological structures.

The frequency region of the human biorhythms includes frequencies in the region of 0–100,000 Hz, or 0–1,000,000 Hz.

Biorhythms of the cells
(generally) 1000–1,000,000 Hz
(as a rule) 1000–100,000 Hz Biorhythms of the organs
(generally) 0.1–1000 Hz
(as a rule) 0.1–200 Hz
(most frequently) 1–100 Hz Biorhythms of individual cell groups
0–0.5 Hz (e.g., skin), and also biorhythms of the individual organ groups of the organism and other biorhythm frequencies of the organism as a whole.

According to this, such a device, with an apparatus for the production of a magnetic field with a static and an alternating field component at the location of the tissue to be treated, is distinguished in that the magnetic alternating field has a predetermined cell biorhythm frequency $v_z$, and is substantially monochromatic, and that the apparatus furthermore includes a device for the amplitude modulation of the magnetic alternating field with a modulation frequency $v_o$, which is set to be equal to the cyclotron resonance frequency $B \cdot q/2 \cdot \eth m$, where B is the static magnetic flux density, q is the charge and m the mass of the predetermined ion, or is equal to a predetermined organ biorhythm frequency or cell biorhythm frequency.

Thus the device according to the invention can be used for simultaneously increasing the internal energy of the cells in the treated region of the intracorporeal electrolyte liquid, and also for increasing the energy of a predetermined group of ions, in order to support the transport of the ions in the region of the cell membrane.

The main concept is the transfer of energy to the cells at the biorhythm frequency $v_z$.

It has been found that not only a magnetic alternating field with the cyclotron resonance frequency can increase the transport of predetermined ions in the region of the cell membranes, but also that this can be attained with an amplitude modulation of a magnetic alternating field, when this oscillates with a biorhythm frequency of cells or organs, and the amplitude is modulated with the cyclotron resonance frequency. The energy transfer with the matching biorhythm frequencies takes place in the treated region according to the following scheme: cells→organ→organ group, with simultaneous action or assistance of the cyclotron resonance on the ion transport.

Besides the direct effects on the energy of an ion through the setting up of the cyclotron resonance frequency associated with this ion by means of the amplitude modulation frequency, in a secondary process the alternating action of this ion with other ions can also increase their energy.

The invention further reflects the inventor's recognition that the effective mechanism of action in a living tissue is propagated starting from individual cells, via the organs, to the organism as a whole. Since a specific cell biorhythm frequency between 1000 Hz and up to $10^6$ Hz can be allocated to specific cells, it is possible to act in a defined manner on a designated kind of cells by means of the production of a magnetic alternating field with a predetermined frequency which corresponds to a given cell biorhythm frequency. This action is also particularly determined in that the alternating field is substantially monochromatic. An undesired action at other frequencies is thereby minimal. The cell biorhythm frequency used, of up to $10^5/10^6$ Hz, which is very high in comparison with the frequencies usually employed, furthermore has the advantage that very high energies can be transferred to the cells in spite of low field amplitudes. This delivery of energy, which can depend on the electrical field of the dame frequency, produced by the high frequency alternating magnetic field, has a resonant course for the selected cells with the cell biorhythm frequency.

A more inclusive and effective magnetic field therapy than with the devices heretofore can be carried out with the device according to the invention, for example, in the field of regressive disorders, inflammations, circulatory disturbances, fractures and traumas, etc.

If the amplitude modulation frequency is situated between 0.1–1000 Hz, set by means of the organ biorhythm frequency, it is insured that corresponding to the recognition of the invention for an optimum action on the human, animal or plant tissue to be treated, the energy delivery is higher by several orders of magnitude at the cell biorhythm frequency, than the energy delivery at the organ biorhythm frequency (the transferred power at a constant amplitude is proportional to the third power of the frequency). To maximize the energy delivery based on the resonance conditions for the cells, the organs or the ions, the device for amplitude modulation can modulate the substantially sinusoidally, in order to attain maximum monochromaticity, but other excitation forms are possible also (rectangular, triangular, trapezoid, sawtooth).

In order to complete the principle of action found by the inventor, starting from the cells to be treated $v_z$ and continuing over the organ $v_o$ to be treated, to the whole organism, the device can furthermore include a device which serves for the amplitude modulation of the magnetic alternating field amplitude modulated with $v_o$, with a frequency which is equal to a predetermined biorhythm frequency $v_R$. This organism biorhythm frequency is generally situated between 0–1000 Hz and thus insures that the energy delivered to the tissue at the organism biorhythm frequency is very much smaller than the energy which is absorbed by the tissue at the organ biorhythm frequency.

Any conventional apparatus can be used for the production of the magnetic alternating fields and/or the static magnetic field. Advantageously, two partial coils are used, which are spaced apart form each other with their longitudinal axes aligned, in order to define between the partial coils an easily accessible space as a treatment space.

In order to make possible a given form of therapy, the devices for the production of the fields can be arranged such that the field vector of the magnetic field which is constant in time substantially coincides with the direction of the field vector of the magnetic alternating field. Thereby, simultaneously in a given frequency interval, different ions can be excited with their cyclotron resonance frequency. In order to make possible another form of therapy, the devices for the production of magnetic fields can be arranged such that the direction of the field vector of the constant magnetic field is situated substantially perpendicular to the direction of the field vector of the magnetic alternating field. It is thereby attained that substantially only one ion or only one organ of the tissue to be treated is supplied with associated energy.

The device can be equipped, according to need, with a number of devices for the production of magnetic alternating fields and static magnetic fields in optional directions. The device thus advantageously includes means for the production of a magnetic alternating field in three mutually perpendicular spatial directions. Furthermore, means to produce static magnetic fields in three mutually perpendicular spatial directions can be included. In this manner, corresponding processes can be caused in optional directions, their actions adding due to the energy delivery caused in the tissue. In order to take account of the effects of the Earth's magnetic field, particularly when low magnetic field strengths are used, the device can include means for the detection of the Earth's magnetic field at the location of the tissue to be treated in dependence on direction, for the setting of the static magnetic field and/or the magnetic alternating field. This adjustment of the device before use to the Earth's magnetic field, or to another static or alternating field disturbance, is then maintained during use. Thus a false value of the cyclotron resonance frequency associated with a kind of ion, or of a biorhythm frequency associated with an organ, can be excluded.

The device for the production of the static magnetic field can be set up such that the static magnetic field is between $10^{-5}$ and 0.1 Tesla at the location of the tissue to be treated. This low flux density makes possible a therapy which corresponds to natural flux densities which are particularly caused by the Earth's magnetic field. Thus, for example, wearers of a heart pacemaker can be given therapy with the device according to the invention without danger. This is particularly so when the amplitude of the magnetic alternating field is also between $10^{-5}$ Tesla and $5 \cdot 10^{-3}$ Tesla; the standard use region is preferably in the region of $1 \cdot 10^{-4}$ Tesla.

In order to be able to flexibly set the device according to the invention to the respective requirements, the device can have an input/output device, a card reader, for example a magnetic card reader or other communication devices such as, for example, a chip card reader or reader for optical data carriers, by means of which the parameters for setting the device can be read in. For setting the device, this card reader can be connected via a controller to a register device, which together with at least one generator can be connected to a modulation unit for the production of a signal to drive the at least one coil which produces the magnetic alternating field. In order to insure as phase synchronous as possible a rectified action on the tissue, mutually associated coils, for example, the partial coils mentioned hereinabove, can be connected to a synchronizing device, which correspondingly controls the at least one generator. In order to drive the coils for the production of a constant magnetic field, the register device can be furthermore connected to a current or voltage source.

BRIEF DESCRIPTION OF THE DRAWINGS

The invention is described hereinbelow with reference to the accompanying drawings.

FIG. 2 schematically shows the time course of the magnetic field for the apparatus shown in FIG. 1, wherein

DETAILED DESCRIPTION OF THE INVENTION

Figure 1:
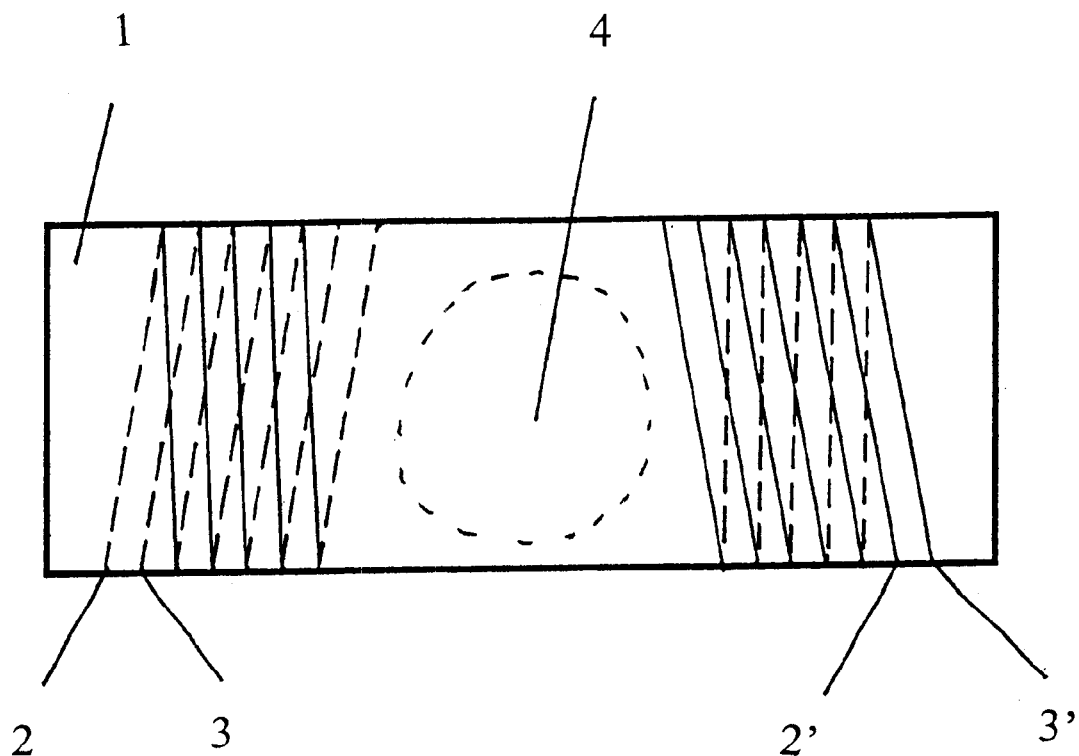
FIG. 1 schematically shows an apparatus of a device according to the invention for the production of a magnetic alternating field and a static magnetic field.

The device for magnetic field therapy of human, animal, and plant tissues, which includes at least a device for the production of a magnetic field with a static component and an alternating field component at the location of the tissue to be treated, is distinguished in that the magnetic alternating field is monochromatic, with a predetermined cell biorhythm frequency $v_z$. The device according to the invention furthermore has a device for the amplitude modulation of the previously described magnetic alternating field with a modulation frequency $v_o$, which is set to be equal either to the cyclotron resonance frequency of a predetermined ion in the tissue or to a predetermined organ biorhythm frequency. The use of the device according to the invention includes the following steps:

1. Selection of the cells to be treated, for example by anamnesis, wherein the designation of the kind of cells to be treated determines the cell biorhythm frequency to be set.
2. Depending on the therapy to be used, choice of the direction and strength of the magnetic alternating field and static magnetic field.
3. Choice of the modulation frequency $v_o$ for the modulation of the magnetic alternating field, wherein, according to the form of therapy, $v_o$ is either the cyclotron resonance frequency of a predetermined kind of ion, or is a predetermined organ biorhythm frequency.
4. Setting the predetermined parameters of the device.

In an embodiment of the invention, the predetermined and adjustable cell biorhythm frequency $v_z$ is between 1000 and $10^6$ Hz. This magnetic field with the cell biorhythm frequency $v_z$ causes an energy uptake in the tissue to be treated, under the assumption of a coil taken arbitrarily, by the induction of a current. The power taken up in the tissue is proportional to the square of the product of the magnetic field amplitude and the frequency.

In an embodiment of the invention, the amplitude modulation frequency $v_o$ in the device is set such that it is determined by the expression $v_o = B \cdot q / 2\delta \cdot m$, where B is the static magnetic flux density, q is the charge and m is the mass of the predetermined ion, the energy of which is to be increased in the scope of employment of the magnetic field. For the purposes of a further form of therapy, the amplitude modulation frequency is set to an organ biorhythm frequency between 0.1 Hz and 1000 Hz, in a specific embodiment of the invention. The magnetic alternating field is modulated substantially sinusoidally by means of the devices for amplitude modulation.

In an embodiment of the invention, the device furthermore includes a device for the amplitude modulation of the magnetic alternating field which is amplitude modulated with $v_o$. This second amplitude modulation is carried out by means of the said device with a predetermined organism biorhythm frequency $V_R$.

Optionally, the signal which arises can again be amplitude modulated, according to the principle of action which was found, with a so-called frequency of the boundary curve.

Figure 2A:
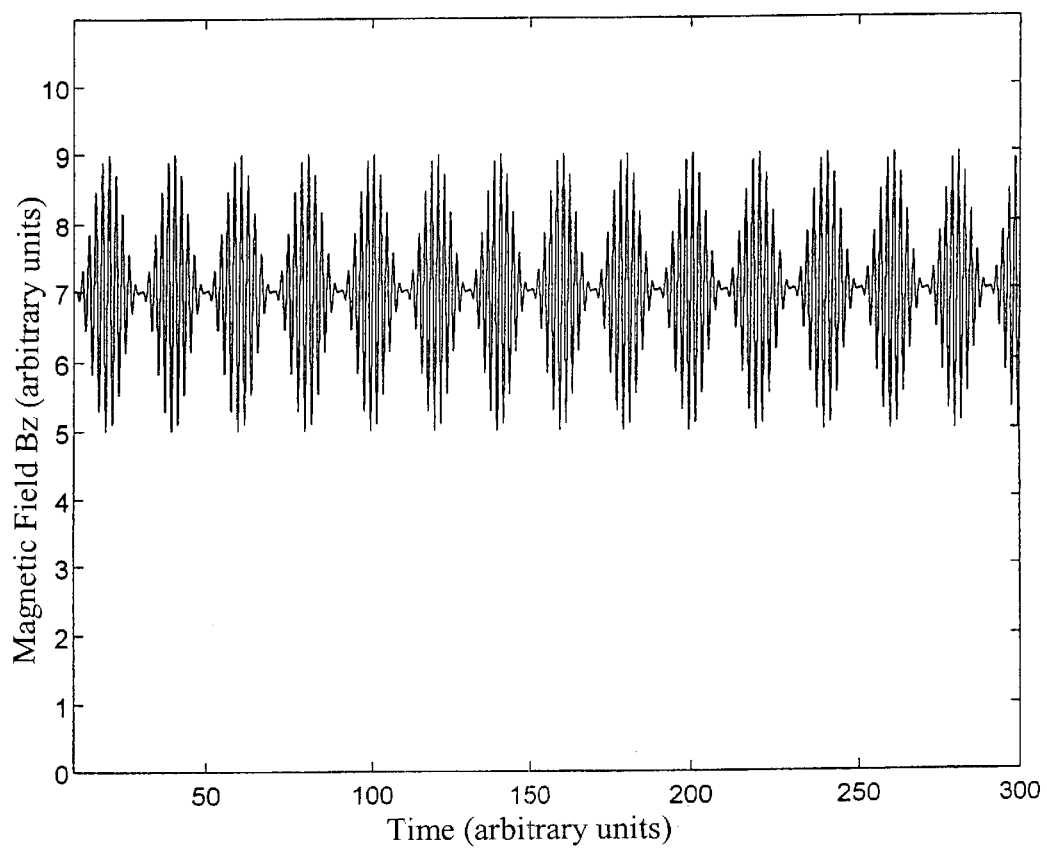
FIG. 2a illustrates the magnetic alternating field with the cell biorhythm frequency $v_z$, modulated with the amplitude modulation frequency $v_o$.
Figure 2B:
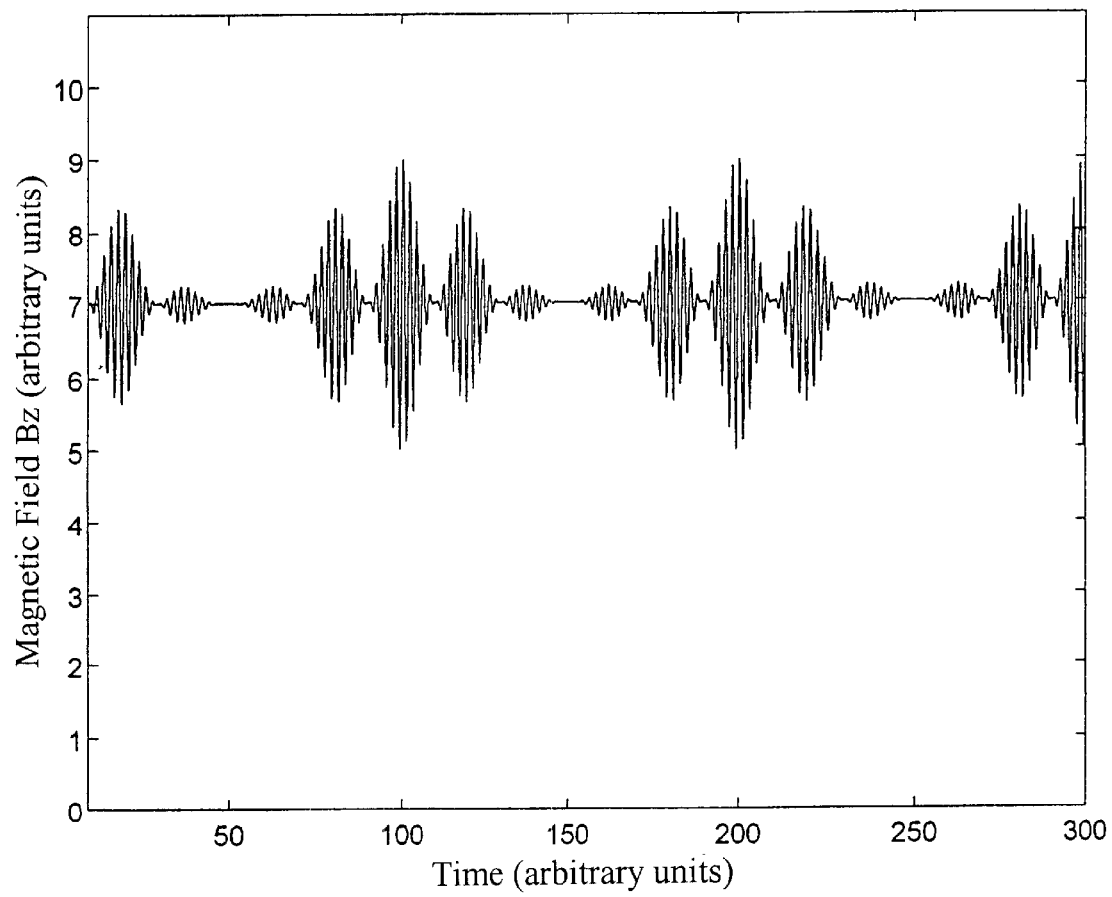
FIG. 2b illustrates the magnetic alternating field of FIG. 2a, wherein this is furthermore modulated with the organism biorhythm frequency $v_R$.

The devices for the production of the magnetic alternating field and/or of the static magnetic field can include, according to the embodiment of the invention, any conventional means for the production of magnetic fields. FIG. 1 shows such an exemplary embodiment, in which two partial coils 2, 2' or 3, 3', which are spaced apart from each other, are arranged on a coil body 1. The adjacent coils 2, 3 or 2', 3' are insulated from each other and are separately electrically driven. The region 4 between the partial coils substantially defines the treatment space, into which the tissue to be treated, for example in the form of a body part, is introduced. For this purpose, the coil body 1 can have a lateral opening, not shown in FIG. 1. Furthermore, the introduction can also be effected along the longitudinal axis of the coil body. The direction of the field vector of the magnetic field which is constant in time is situated parallel to the field vector of the magnetic alternating field, in the exemplary embodiment of the invention shown in FIG. 1. The resulting magnetic field in the region 4 is schematically shown in FIGS. 2a and 2b, the Z axis being taken in the longitudinal direction to the coil body. FIG. 2a shows the resulting magnetic field Bz in the Z-direction in dependence on time, for a monochromatic magnetic alternating field which has a predetermined cell biorhythm frequency and which is modulated with an amplitude modulation frequency, the modulation frequency being very much smaller than the cell biorhythm frequency. FIG. 2b shows the course of the magnetic field in the Z-direction in dependence on time, for the case in which, in addition to the amplitude modulation with the frequency $v_o$, the resulting magnetic field is further amplitude modulated, now with the organism biorhythm frequency $v_R$, which is at most 0.5

Hz. FIG. 2a thus illustrates an oscillation which is composed of three parts: the basic oscillation with the carrier frequency $v_z$ and oscillations of the two sidebands with $v_z-v_o$ and $v_z+v_o$.

However, embodiments of the invention are not limited to cases in which the field vectors of the magnetic field which is constant in time and of the static magnetic field coincide. In a series of embodiments of the invention, the coils for the production of the magnetic fields are arranged such that the field vector of the static magnetic field is perpendicular to the field vector of the magnetic alternating field.

An embodiment of the invention which can be most flexibly matched to the requirements at any given time includes means for the production of a magnetic alternating field in three mutually perpendicular spatial directions and means for the production of a static magnetic field in three mutually perpendicular spatial directions. In this case, there are in all preferably 15 coils, each of which includes two partial coils installed in a suitable manner on a coil body, and connected such that the treatment space again results between the partial coils. Numerous magnetic field configurations can be produced by suitable and selected excitations of the coils. In addition to the already described arrangement, in which a static and a magnetic alternating field are produced in the Z-direction, the magnetic alternating field being for example modulated with the cyclotron resonance frequency, which depends on the static magnetic field: instead of the alternating field in the Z-direction, however, there can also be used an alternating field in the Y-direction, in the X-direction, or simultaneously in the X- and Y-directions. The frequency of the respective fields is set to the selected cell biorhythm frequency. In the same way, the alternating fields in the respective directions are modulated with the cyclotron resonance frequency or with the organ biorhythm frequency. A configuration is furthermore possible in which a static field is set in the Z-direction and a magnetic alternating field is excited with the allocated amplitude modulations in all three spatial directions X, Y, Z. In the general case, both static magnetic fields and also amplitude modulated magnetic alternating field are produced in all three spatial directions.

Static magnetic fields with a flux density of $10^{-5}$ Tesla to 0.1 Tesla are produced by means of the device according to the invention. There then results at a flux density of $10^{-4}$ Tesla, for example, for a $H^+$ cyclotron resonance frequency of 1528 Hz, for $Li^+$ 218.3 Hz, while the frequencies for heavier ions are very much lower, for example $K^+$ 38.4 Hz and $Cu^+$ 24 Hz.

| Ions, chemical elements | Frequencies(Hz) for $B = 1\ 10^{-4}$ T; 1 G | Frequencies(Hz) for $B = (0.2-0.7)\ 10^{-4}$ T |
|---|---|---|
| H $(1)^+$ | 1528 | 305.6–1070 |
| O $(16)^{2-}$ | 191 | 38.2–133.7 |
| Na $(23)^{30}$ | 66.4 | 13.3–46.5 |
| P $(31)^{3+}$ | 147.9 | 29.4–103 |
| P $(31)^{5-}$ | 246.5 | 49.3–172.6 |
| K $(40)^+$ | 38.4 | 7.68–26.91 |
| Mn $(55)^{2+}$ | 55.6 | 11.2–38.92 |
| Fe $(56)^{3+}$ | 81.19 | 16.38–57.33 |
| Fe $(56)^{2+}$ | 54.6 | 10.92–38.22 |
| Cu $(64)^+$ | 24 | 4.8–16.8 |
| Se $(79)^{2-}$ | 38.8 | 7.76–27.16 |
| Br $(80)^-$ | 19.1 | 3.82–13.4 |
| Ag $(108)^+$ | 14 | 2.8–9.9 |
| J $(126)^-$ | 12.13 | 2.4–8.5 |
| Au $(197)^+$ | 7.8 | 1.56–5.5 |

This Table shows the possibility of simultaneous action on the organs and ions in the organ biorhythm frequency region 1–200 Hz with $B_z=0.2-1$ G and on protons in the frequency region of 300–1530 Hz with $B_z=0.2-1$ G.

The magnetic alternating field, which has the cell biorhythm frequency, is amplitude modulated, as described hereinabove, with cyclotron resonance frequencies calculated in this manner. The amplitude of the magnetic alternating field is, like the static magnetic field, adjustable between $10^{-5}$ Tesla and $7 \cdot 10^{-4}$ Tesla.

The amplitude can however be greater, according to requirements.

In an embodiment, the device includes a device for the detection, in dependence on direction, of the magnetic field present at the location of the tissue to be treated; for example, a magnetometer. The detected magnetic field is now taken into account for the setting of the static magnetic field before the treatment, in accordance with the chosen therapy. If for example a static magnetic field of $10^{-4}$ Tesla in the Z-direction is to be used, the Earth's magnetic field in this direction however amounts to $5 \cdot 10^{-6}$ Tesla, so the respective coil is caused to respond so that it produces a static magnetic field of $1.5 \cdot 10^{-5}$ Tesla with reversed sign, or $1.5 \cdot 10^{-5}$ Tesla with the direct sign. In the same manner, the components of the Earth's magnetic field in the X- and Y-directions can be taken into account or compensated, and kept constant during operation.

Figure 3:
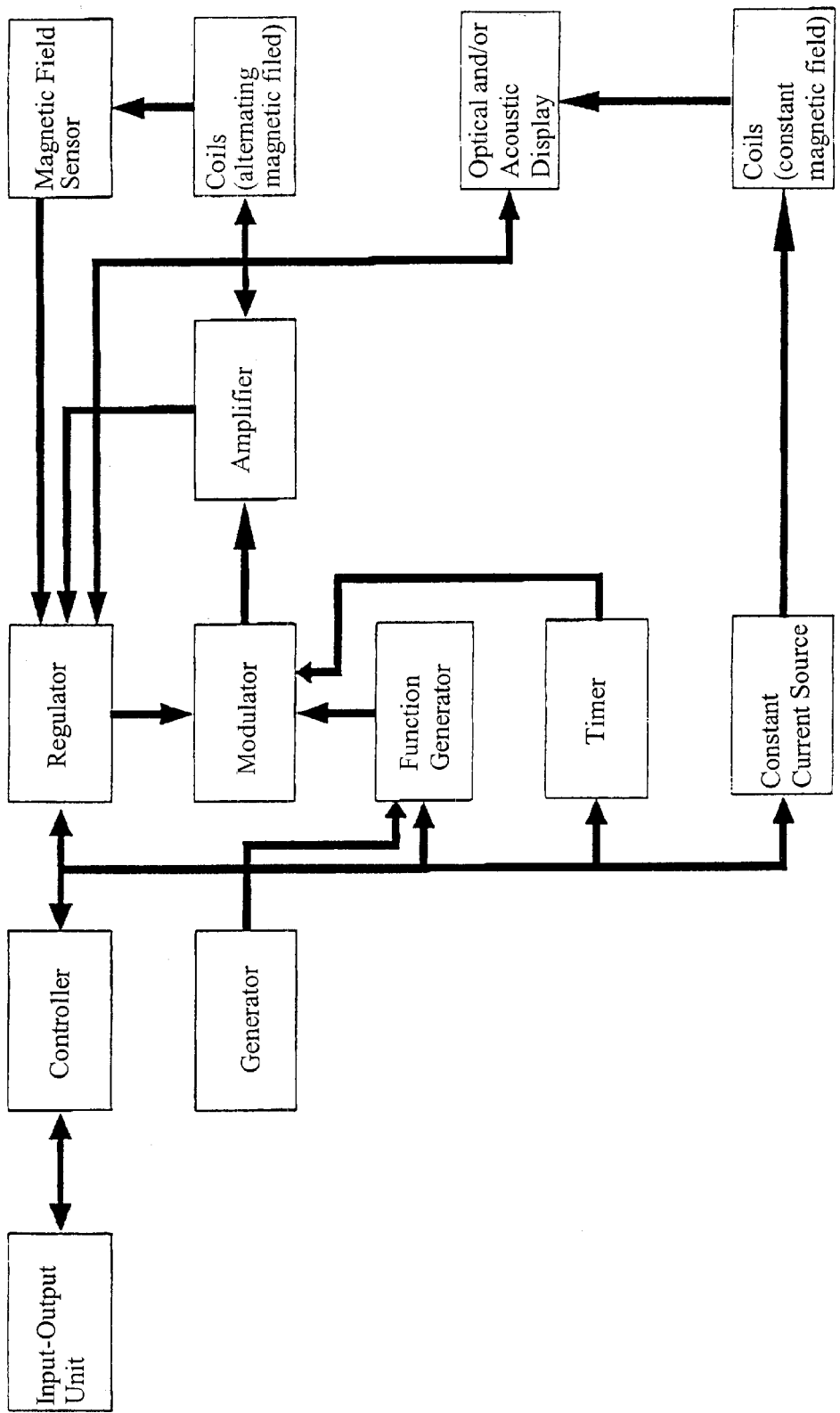
FIG. 3 shows a block circuit diagram of an exemplary embodiment of the invention.

The structure of an embodiment of the invention is described in FIG. 3 in the form of a block circuit diagram. Accordingly, the device has a card reader, by means of which the parameters for setting the device are read in. This concerns, for example, data on the cell biorhythm frequency, the cyclotron resonance frequency, or the organ biorhythm frequency, the organism- or cell-biorhythm frequency, and the flux densities of the individual magnetic fields to be produced in the different directions. The card reader is connected via a controller to a register device in which the read-in parameters are stored. The register device is connected, together with the generator or the generators, to a modulation unit for the production of a signal for driving the coil which produces the magnetic alternating field. If several coils are included for the production of an alternating magnetic field, the device according to the invention can also have several modulation units allocated to the respective coils. In order to insure an in-phase driving of the individual coils for the production of an alternating magnetic field, the coils are connected to the generator or generators via a synchronizing unit. The device according to FIG. 1 furthermore includes a voltage source which can equivalently also be embodied by a current source, which is driven by means of the register and provides a constant voltage or a constant current for the excitation of the coil for the production of a static magnetic field.

For the production of the monochromatic oscillations having the cell biorhythm frequency, there is used in the corresponding device, according to the embodiment of the invention, a voltage resonance (series connection of an inductance and a capacity) or a current resonance (parallel connection of an inductance and a capacity). This LC circuit is then respectively tuned to the predetermined cell biorhythm frequency. The production of the modulation frequencies, i.e., the organ biorhythm frequency, the cyclotron resonance frequency, or the organism biorhythm frequency, is produced in associated LC circuits in the same manner.

I claim:
1. Device for magnetic field therapy of human, animal, and plant tissues, which includes at least a device for the production of a magnetic field with a static component which is constant in time and an alternating field component at the location of the tissue to be treated, characterized in that the magnetic alternating field has a predetermined cell biorhythm frequency $v_z$ and is substantially monochromatic, and the device furthermore includes a device for the amplitude modulation of the magnetic alternating field with a modulation frequency $v_o$ which is determined by the expression $v_o = Bq/2\delta m$, wherein B is the static magnetic flux density, q is the charge and m the mass of the predetermined ion, or is a predetermined organ biorhythm frequency.

2. Device according to claim 1, characterized in that the predetermined cell biorhythm frequency $v_z$ is situated between 1000 Hz and $10^6$ Hz.

3. Device according to claim 1, characterized in that the amplitude modulation frequency set by means of the organ b lies between 0.1 Hz and 1000 Hz.

4. Device according to claim 1, characterized in that the device for amplitude modulation modulates the magnetic alternating field substantially sinusoidally.

5. Device according to claim 1, characterized in that the device furthermore includes a device for the amplitude modulation of the magnetic alternating field modulated with $v_o$ with a frequency which is equal to a predetermined organism biorhythm frequency $v_R$.

6. Device according to claim 1, characterized in that a device for the production of the magnetic alternating field and/or of the static magnetic field includes two mutually spaced apart partial coils with mutually aligned longitudinal axes.

7. Device according to claim 1, characterized in that the direction of the field vector of the magnetic field which is constant in time substantially coincides with the direction of the field vector of the magnetic alternating field, at least at the location of the tissue to be treated.

8. Device according to claim 1, characterized in that the direction of the field vector of the magnetic field which is constant in time is substantially perpendicular to the direction of the field vector of the magnetic alternating field, at least at the location of the tissue to be treated.

9. Device according to claim 1, characterized in that means for the production of a magnetic alternating field in three mutually perpendicular spatial directions is included.

10. Device according to claim 1, characterized in that means for the production of a static magnetic field in three mutually perpendicular spatial directions is included.

11. Device according to claim 1, characterized in that the device includes means for the detection, in dependence on direction, of the Earth's magnetic field present at the location of the tissue to be treated, and for taking account of the detected Earth's magnetic field for the setting of the static magnetic field before the production of the static magnetic field and./or of the magnetic alternating field.

12. Device according to claim 1, characterized in that the static magnetic field is between $10^{-5}$ Tesla and $7 \cdot 10^{-4}$ Tesla.

13. Device according to claim 1, characterized in that the amplitude of the magnetic alternating field is between $10^{-5}$ Tesla and $7 \cdot 10^{-4}$ Tesla.

14. Device according to claim 1, characterized in that the device has a card reader, by means of which parameters for the setting to the device are read in.

15. Device according to claim 14, characterized in that the card reader is connected via a controller to a register device which, together with at least one generator, is connected to a modulation unit for the production of a signal for driving the at least one coil, which produces the magnetic alternating field.

16. Device according to claim 15, characterized in that mutually associated coils are connected to a synchronizing device which controls the at least one generator such that the coils are driven substantially in-phase.

17. Device according to claim 15, characterized in that the register device is further connected to a voltage source which drives at least one coil for the production of a constant magnetic field.

* * * * *